Fidelio
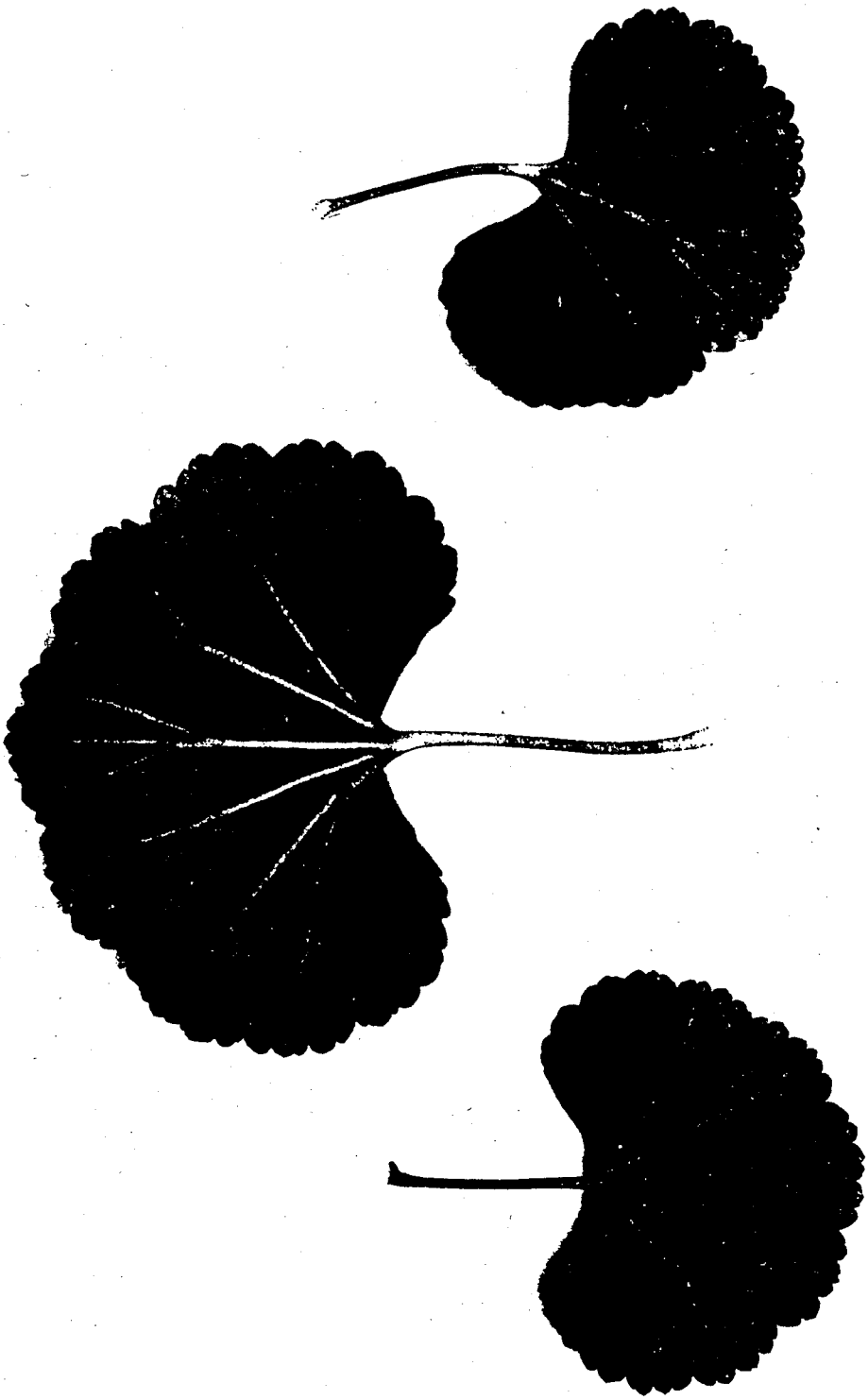

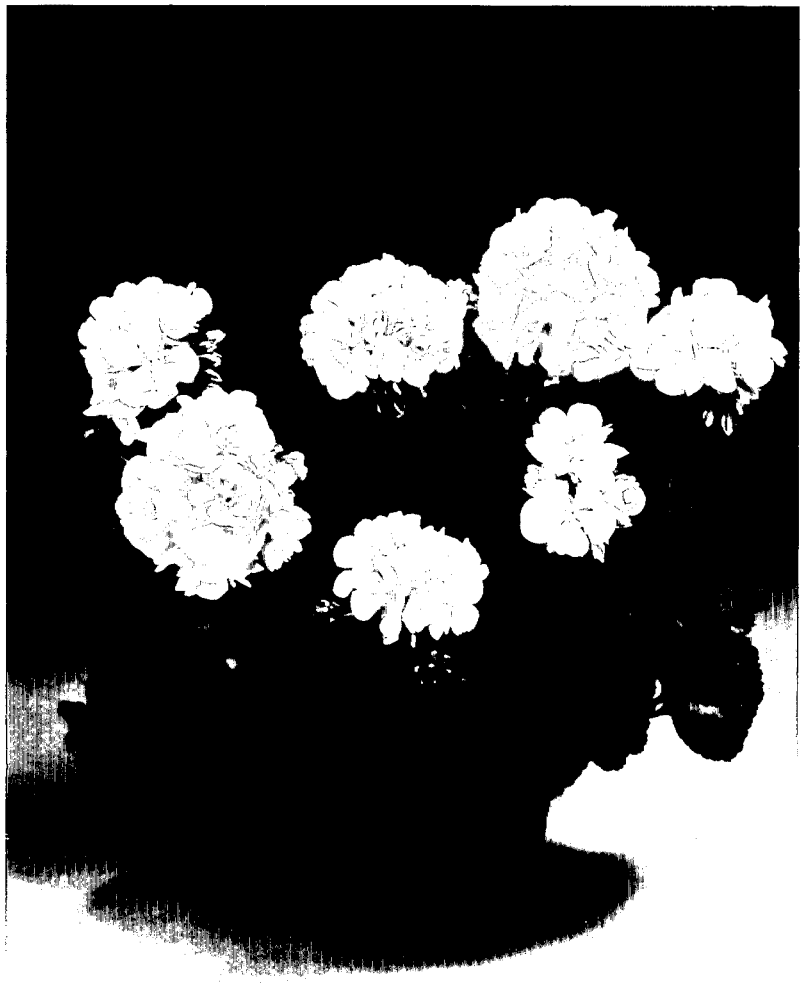

United States Patent [19]

Schumann

[11] Patent Number: Plant 5,752

[45] Date of Patent: Jun. 24, 1986

[54] GERANIUM PLANT NAMED FIDELIO

[75] Inventor: Ingeborg Schumann, Bad Ems, Fed. Rep. of Germany

[73] Assignee: Fischer Geraniums, Inc., Netherlands Antilles

[21] Appl. No.: 644,448

[22] Filed: Aug. 27, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of geranium plant named Fidelio, particularly characterized by its salmon-pink flower color, early flowering response, fast rooting, excellent branching, superior summer flower production, and its low temperature tolerance.

2 Drawing Figures

1

The present invention comprises a new and distinct cultivar of geranium, botanically known as *Pelargonium zonale,* and hereinafter referred to by the cultivar name Fidelio.

Fidelio is a product of planned breeding program which had the objective of creating new geranium cultivars with salmon-pink flower color, semi-double flower form, short plant height, fast rooting habit, good branching, durable flowers, good temperature tolerance, and eary spring flowering response.

Fidelio was originated from a hybridization made in a controlled breeding program in Hillscheid, Federal Republic of Germany in 1979. The female parent was the unpatented cultivar Springtime Irene, principally characterized by its salmon, semi-double flowers, good zonation in the foliage, and poor resistance to rain. The male parent of Fidelio was Achspen, an unpatented cultivar principally characterized by its light salmon, semi-double flowers, lack of zonation in the foliage, and compact growth habit.

Fidelio was discovered and selected as one flowering plant within the progeny of the stated cross by Ingeborg Schumann on June 27, 1980 in a controlled environment in Hillscheid, Federal Republic of Germany.

The first act of asexual reproduction of Fidelio was accomplished when vegetative cuttings were take from the initial selection in January 1981 in a controlled environment in Hillscheid, Federal Republic of Germany by a technician working under formulations established and supervised by Ingeborg Schumann. Horticultural examination of selected units initiated in spring of 1981 and continuing in 1982 has demonstrated that the combination of characteristics as herein disclosed for Fidelio are firmly fixed and are retained through successive generations of asexual reproduction.

Fidelio has not been observed under all possible environmental conditions. The phenotype may vary significantly with variations in environment such as temperature, light intensity, and day length. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fidelio which in combination distinguish this geranium as a new and distinct cultivar.

2

1. Salmon-pink flower color, commonly characterized in begonia cultivars.
2. Slight foliage zonation.
3. Early spring flowering response.
4. Very fast rooting.
5. Cultivation can be carried out at temperatures below 12° C.
6. Excellent branching.
7. Stable peduncles in different climates.
8. Superior summer flower production.

Of the many commercial cultivars known to the present inventor, the most similar in comparison to Fidelio are the unpatented cultivars Salmon Irene and Springtime Irene. Reference is made to attached Chart A which compares certain characteristics of Fidelio to those same characteristics of Salmon Irene and Springtime Irene. In general comparison to Salmon Irene, Fidelio has faster rooting, better branching, shorter internode length, and shorter plant height. In comparison to Springtime Irene, Fidelio has smaller leaves, better rain resistance, better branching, faster rooting and better temperature tolerance.

The accompanying photographic drawings show typical flower and foliage characteristics of Fidelio, with colors being as true as possible with illustrations of this type. Sheet 1 comprises a color photograph showing a perspective view of the plant. Sheet 2 is a black and white print of the underside of leaves at two stages of growth.

In the following description color references are made to The Horticultural Colour Chart (HCC). The color values were determined between noon and 2 p.m. on June 26, 1984 under 25,000 LUX at Hillscheid, Federal Republic of Germany.

Classification:

*Botanical.*—A hybrid of the genus *Pelargonium L'Hert.*

*Commercial.*—Fidelio.

I. Inflorescence:

A. *Umbel.*—Average diameter: 107 mm. Average depth: 79 mm. Peduncle length: 208 mm. Pedical length: 25 mm. with ⅓ strength anthocyan at an open corolla.

B. *Corolla.*—Average diameter: 47 mm. Form: Semi-double. Color (General tonality from a distance of three meters): HCC 619/1. Color (upperside): HCC 619/1. Color (underside): HCC 620/1.

C. *Bud.*—Shape: Elliptic. Color: Nearly white.

D. *Reproductive organs.*—Androecium: Monodelphous, 8–9 stamens, sometimes grown together; moderate pollen. Gynoecium: 5–6 lobed stigma, style and stigma color red.

E. *Spring flowering response period.*—In Hillscheid, Federal Republic of Germany in 1982, 55% of plants with at least 1 flower opened 13 weeks after planting unrooted cutting.

F. *Outdoor flower production.*—The flower count in 1982 in Hillscheid was between 61 and 71 flowers per plant for June through October observation.

G. *Durability.*—Shatter and rain resistance very good.

II. Plant:

A. *Foliage.*—Form: Cross-elliptic. Margin: Crenate. Color (upper side): Medium green. Color (underside): Medium green. Color (zonation): Faint zonation. Tolerance of botrytis: Good to medium.

B. *General appearance and form.*—Internode length: 36 mm. Branching pattern: An average of 4 branches per plant being produced. Height: 260 mm.

CHART A

| CULTIVAR | Branching Habit (number of branches of non-pinched plants 13 weeks after planting unrooted cutting) | Corolla Color |
|---|---|---|
| SPRINGTIME IRENE | 3.3 | RHS 52D |
| SALMON IRENE | 3.0 | RHS 44D |
| FIDELIO | 4.0 | HCC 619/1 |

| | Plant Height | Outdoor Flowering Response per plant for June to October |
|---|---|---|
| SPRINGTIME IRENE | medium | 55–57 |
| SALMON IRENE | tall | 45–49 |
| FIDELIO | medium | 61–71 |

| CULTIVAR | Hillscheid Spring Flowering Response | Internode Length |
|---|---|---|
| SPRINGTIME IRENE | 35% (late) | medium |
| SALMON IRENE | 50% (early) | long |
| FIDELIO | 55% (early) | medium |

| | Zonation of Foliage | Rooting Time |
|---|---|---|
| SPRINGTIME IRENE | good | medium |
| SALMON IRENE | medium | slow |
| FIDELIO | faint | very fast |

I claim:

1. A new and distinct cultivar of geranium plant named Fidelio, as described and illustrated, and particularly characterized by its salmon-pink flower color, early flowering response, fast rooting, excellent branching, superior summer flower production, and its low temperature tolerance.

* * * * *